United States Patent [19]
Pelak

[11] Patent Number: 5,556,280
[45] Date of Patent: Sep. 17, 1996

[54] METHOD AND APPARATUS FOR APPLIANCE MOUNTING

[76] Inventor: Mark S. Pelak, 914 SW. Santa Barbara Pl., Cape Coral, Fla. 33941

[21] Appl. No.: 251,598

[22] Filed: May 31, 1994

[51] Int. Cl.⁶ .................................................. A61C 8/00
[52] U.S. Cl. ........................... 433/172; 433/173; 433/220
[58] Field of Search ..................................... 433/169, 172, 433/173, 181, 174, 220

[56] References Cited

U.S. PATENT DOCUMENTS

| | | | |
|---|---|---|---|
| 3,797,114 | 3/1974 | Wiland | 32/12 |
| 4,431,416 | 2/1984 | Nisnick | 433/174 |
| 4,540,367 | 9/1985 | Sulc | 433/181 |
| 4,681,542 | 7/1987 | Baum | 433/172 |
| 4,850,873 | 7/1989 | Lazzara et al. | 433/220 |
| 5,073,111 | 12/1991 | Daftary | 433/173 |
| 5,169,308 | 12/1992 | Kvist | 433/173 |

*Primary Examiner*—Cary E. O'Connor
*Attorney, Agent, or Firm*—Myron E. Click

[57] ABSTRACT

Method and apparatus for removably mounting a dental appliance in a mouth. An abutment member has a tapered support surface which extends away from the affixation area of the abutment. The tapered support surface is formed to be received in and mate with a complementary surface formed in an appliance to provide co-acting support surfaces for the appliance, so that the appliance need not depend upon gum tissue for support thereby enabling design of an appliance to fully conceal the area of affixation for esthetic appearance while providing the look of natural teeth. First and second coupling devices are adapted to be respectively secured to the abutment member and the appliance for removably retaining an appliance on the abutment member.

20 Claims, 1 Drawing Sheet

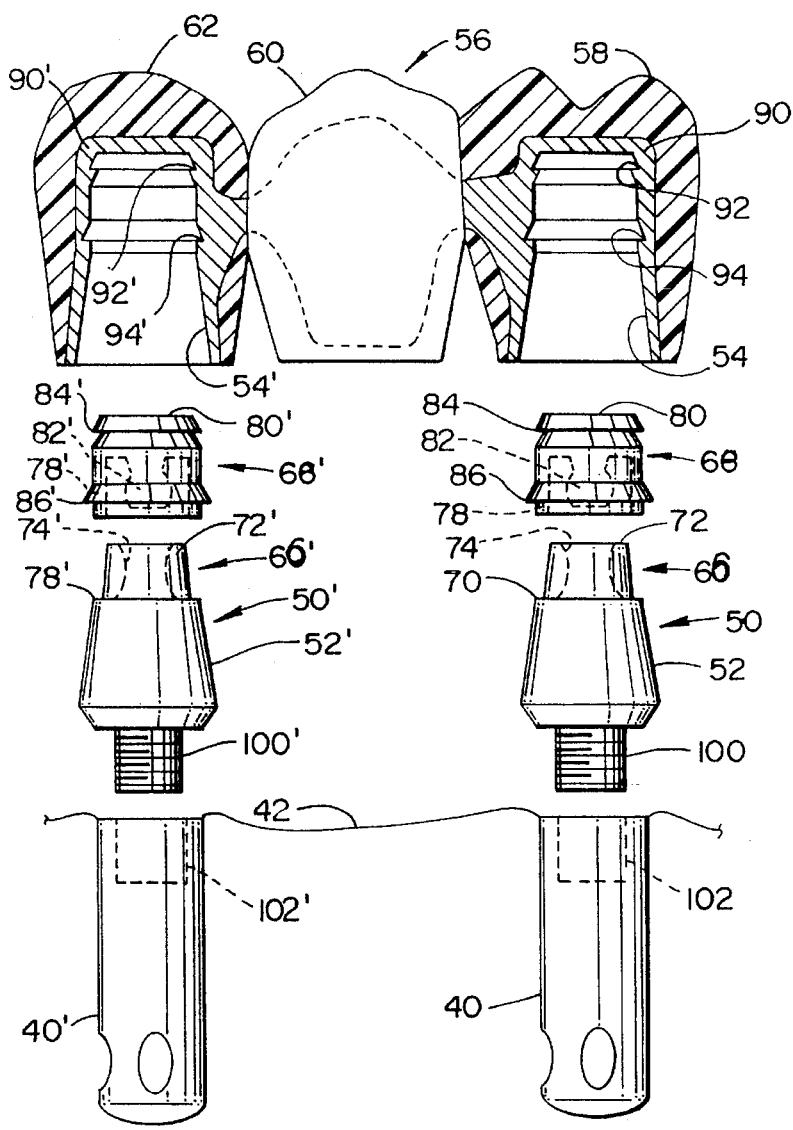
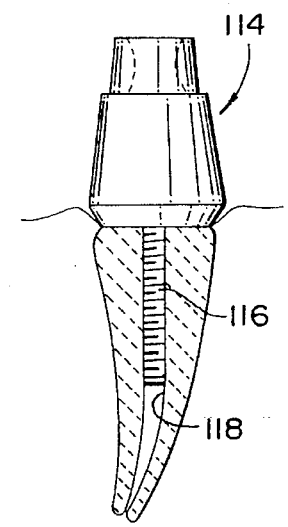
Fig- 4
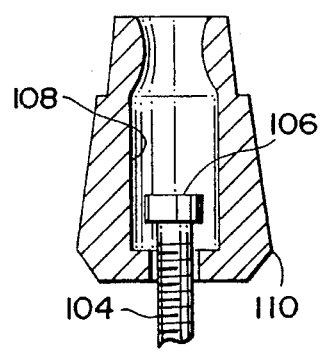
Fig- 5
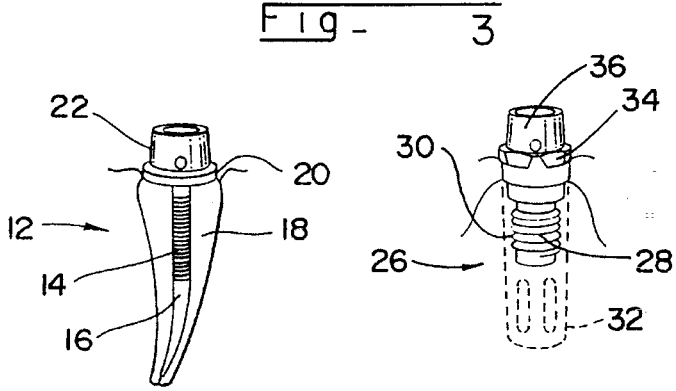
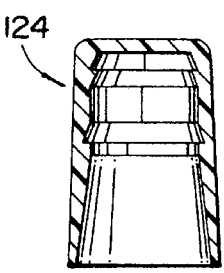
Fig- 6

METHOD AND APPARATUS FOR APPLIANCE MOUNTING

BACKGROUND OF THE INVENTION

1. Field of the Invention

This invention relates to dental appliance mounting generally and, in particular, to a method and apparatus for removably mounting a dental appliance, such as an artificial tooth, a full or partial denture, a bridge or other appliance in a mouth.

2. Description of the Prior Art

Replacing lost teeth has been the subject of continuing research over the years. The use of complete or removable partial dentures, with clasps or other attachment means for connection to abutment teeth, is still probably the leading approach being used. However, the stability of such dentures is a problem. There can also be a problem with comfort and food impaction between the gingiva and the underside of the denture base. Further, there can be physical and psychological adjustments for those who have difficulty with bulky removable dentures.

U.S. Pat. No. 3,797,114, issued Mar. 19, 1974 discloses a detachable mount for a dental cap and bridge in an attempt to solve the problems discussed above. This involved preparation of a tooth (or teeth) in the same manner as is commonly employed for attaching a permanent cap. However, instead of directly attaching a cap, a coping is fitted and permanently attached to the prepared tooth. One half of a fastening means is secured to the top of the coping. Then a conventional cap with an undersocket sized to fit over the coping is prepared. The remaining half of the fastener is secured in the undersocket to provide a removably retained cap.

While this was an improvement over the prior art at that time, there is still a problem with thoroughly cleaning and keeping healthy the gingival tissues surrounding the base of the coping. Sometimes a complete seating of the coping is not always obtained. Moreover, once the coping has been permanently installed it is most difficult to remove it without damaging either the coping or the prepared part of the tooth beneath it, in the event that decay or other problems occur as a result of an incomplete seal by the cement underneath the coping or other problems that arise.

Dental implants have also become a viable alternative for replacing lost teeth, and offer solutions to patients who can physically accept such implants. However, present implants and appliances do not always completely meet the needs and requirements of a patient.

Dental implants are presently used to support conventional dental appliances having a saddle that overlies and is at least partially supported by gum tissue. Such dental appliances can be permanently or removably connected to the implants. The removable connections may use tiny screws through the appliance to fasten it to implants. Thus the appliance normally must be removed by a dentist. As a result, the appliance is not removed for cleaning and tissue stimulation for extended periods resulting in damage as discussed above.

Alternatively, a so-called implant abutment can be used which can be screwed into a dental implant, and which carries only a coupling means directly on top of the abutment. Since only the coupling means is available for contact with the abutment, a saddle in contact with the gum must be used for support of the appliance and to provide stability to the appliance.

A direct overdenture is also commercially available in a form similar to the implant abutment discussed in the previous paragraph, However, instead of being screwed into a dental implant, this overdenture is provided with a steel shaft for direct cementation in a bore formed in a tooth root. As in the case of the implant abutment in the preceding paragraph, only a coupling means is carried on the top of the direct overdenture. Therefore, a saddle must be used for the appliance to rest on the gum for support and stability.

Thus, a conventional "fixed bridge" is permanently fixed in placed. The "fixed removable bridge" attached by screws must be removed by a dentist. Present implant abutments and direct overdentures require the use of saddles on the appliance. None of these is the best solution.

Bridges and other appliances may be formed to allow access for tissue stimulation and food removal. However, the appliance must be contoured to provide thin necks around tissue areas with open spaces or embrasures between for hygenic purposes. Such appliances have a poor esthetic appearance and still act as food traps.

Esthetics is also a problem with appliances with saddles over gum tissue, and patients may object to their appearance. This is true whether or not the appliance is removable by the patient.

U.S. Pat. No. 4,431,416, issued Feb. 14, 1984 discloses a dental implant system in which a pillar in the upper part of the implant can provide a platform for a coupling device to removably retain an appliance on the implant. However, the appliance 18 requires a saddle resting on gum tissue to insure that bite force is transmitted via the denture to the gum tissue 42, by-passing the implant in the transmission of such force (as noted in Column 6, lines 1 to 6). As noted above the use of a saddle is objectionable, because of appearance, food impaction, etc.

U.S. Pat. No. 4,431,416 also discloses in FIGS. 12 and 13 the use of a pillar 94 that has a frusto-conical head 96 that corresponds to a prepared tooth 92. This plastic version of an implant abutment provides permanent support for a fixed bridge or other appliance that is cemented to head 96, and thus is not removable by the patient.

In addition to the pillar abutment shown in U.S. Pat. No. 4,431,416 just discussed, a conventional implant abutment that has a coupling means associated with it is commercially available from APM-Sterngold. The Sterngold abutment has a threaded shaft attached to the base of the abutment to be received by a threaded bore in a dental implant. The Sterngold abutment discloses a tapered surface extending away from the affixation area. However, this tapered surface is formed only on part of one half of a coupling means and serves only to guide a cup holding the male portion of the coupling means into a seated position on the tapered surface of the one half. Thus, the Sterngold tapered surface does not and cannot directly support an appliance.

Moreover, the Sterngold implant abutment is used to support removable appliances which have a saddle designed to rest on and be supported by gum tissue. The saddle transmits the bite force to the gum tissue and provides stability to the appliance. However, saddles have problems as discussed herein.

SUMMARY OF THE INVENTION

Other known prior art in this area includes saddles or other unacceptable features as discussed hereinbefore. To resolve those problems, this invention is directed to a "fixed removable bridge". That is, an abutment is provided which has an extended tapered surface for directly supporting an appliance. The tapered surface is formed to be received in and mate with a complimentary surface formed in an appliance. Thus, the appliance is fully supported by the tapered surface of the abutment and need not depend upon gum tissue for support. This enables design of an appliance to look like a natural tooth or teeth, and to nestle close to the gum to fully conceal the area of abutment affixation and the abutment to provide the look of natural teeth.

First and second coupling means or devices are respectively secured to the abutment of this invention and the appliance, and removably retains the appliance on the tapered support surfaces of the abutment. The coupling means preferably provides a cushioned flexible connection to reduce bite force transmission to the abutment support. The mating of the tapered support surface of the abutment with the complimentary receiving surface of an appliance accurately guides the coupling means into a coupling relationship to removably retain the appliance. This permits removal of the appliance by the patient for hygenic and tissue stimulation purposes, in the area concealed by the appliance, on a regular tooth brushing schedule.

Therefore, in contrast to the coping/cap arrangement discussed above, this invention not only enables the design and placement of false teeth that have a natural appearance in place in the mouth, but also provides ready access to the affixation area. This access not only enables easy removal by the patient for gum stimulation and hygenic purposes, but also enables repair and orthodontic restoration of an existing replacement tooth or teeth. Further, a tooth root or partial tooth serving as a support for this invention's abutment member, which can be made removable, can be easily accessed to treat the tooth without endangering the tooth by removal of a permanently cemented coping. Similarly, when this invention's abutment is used with a dental implant, access to the implant is readily available for repair, treatment or other correction.

In any of the above situations, if replacement of the abutment member is indicated, it is more readily accomplished at less expense than prior art approaches.

Accordingly, it is an object of this invention to provide an improved method and apparatus for mounting dental appliances.

It is a further object of this invention to provide such method and apparatus which will enable design of an appliance which can be removed by the wearer without going to the dentist, yet which looks like natural teeth while fully concealing the affixation area.

A still further object of this invention is to provide such method and apparatus in which the dental appliance is fully supported by the abutment of this invention and need not depend upon gum tissue for support, thus avoiding food impaction problems.

Other objects, advantages and features of this invention will become apparent when the following description is taken in conjunction with the accompanying drawings.

BRIEF DESCRIPTION OF THE DRAWINGS

FIGS. 1 and 2 illustrate two embodiments of the prior art which are not shown in the search patents forwarded with this application, FIG. 3 is a side elevational exploded view, partially in section, of the components of this invention, FIG. 4 illustrates a second embodiment of this invention, FIG. 5 illustrates a second apparatus for affixing the abutment members in FIG. 3 to dental implants, and FIG. 6 is a sectional view of an additional component of this invention.

DESCRIPTION OF THE PREFERRED EMBODIMENTS

FIGS. 1 and 2 illustrate a direct overdenture attachment and an implant abutment attachment. These attachments are commercially available from APM-Sterngold. Both attachments are functionally satisfactory for the intended purposes. However, they do have problems because they require the use of saddles on the dentures, as discussed in detail hereinbefore under the Description of the Prior Art. They are shown in the drawings to point out the difference between them and the abutment members of this invention.

In FIG. 1 a direct overdenture, generally indicated at 12, has a steel shaft 14 for direct cementation in a bore 16 formed in a tooth root 18. A platform 20 is carried on the top of shaft 14 and supports the female half 22 of a removable coupling means. The male half is not shown here because a suitable male half is illustrated and described in FIG. 3. The sides of the platform 20 are usually substantially vertical and extend upwardly for the distance desired to provide a gingival cuff. That distance may be changed to accomodate variable gingival thickness. The inward taper extending upwardly of the female half of the coupling means serves to guide the male half into a coupling relationship. This tapered surface serves only for guidance purposes and provides no direct support for an appliance being removably secured to the overdenture. As noted herein, support for the appliance is provided by a saddle thereon, which rests directly on the gingival or gum tissue.

In FIG. 2, an implant abutment attachment is generally indicated at 26, and has a steel shaft 28 which is threaded to be received in a threaded bore 30 formed in a dental implant 32. A platform 34 carried on top of shaft 28 supports the female half 36 of a coupling means. As with the overdenture attachment in FIG. 1 a gingival cuff of variable height is provided. As also provided in the overdenture of FIG. 1, the female coupling means has an inward taper extending upwardly to guide the male half into a coupling relationship. This tapered surface serves for only guidance purposes and provides no direct support for an appliance being removably secured to the overdenture. As noted herein, support for the appliance is provided by a saddle thereon, which rests directly on the gingival or gum tissue.

In FIG. 2, an implant abutment attachment is generally indicated at 26, and has a steel shaft 28 which is threaded to be received in a threaded bore 30 formed in a dental implant 32. A platform 34 carried on top of shaft 28 supports the female half 36 of a coupling means. As with the overdenture attachment in FIG. 1, a gingival cuff of variable height is provided. As also provided in the overdenture of FIG. 1, the female coupling means has an inward taper extending upwardly to guide the male half into a coupling relationship. This tapered surface serves only for guidance and provides no direct support for an appliance being removably secured to the implant abutment. Again, the support for an appliance is provided by a saddle thereon, which rests directly on the gum tissue.

Referring now to FIG. 3, two dental implants 40 and 40' are installed in a jaw bone (not shown) in a conventional manner. The gum tissue line is indicated at 42.

The first embodiments of this invention's abutment members are shown at 50 and 50', and have tapered support surfaces 52 and 52' which extend away from the area of affixation on one jaw toward the opposing jaw. The tapered support surfaces 52 and 52' are formed to be received in and mate with complementary surfaces 54 and 54', respectively, formed in an appliance 56 to provide direct support for such appliance. Thus, the appliance 56 does not need or depend upon gum tissue for support. This enables design of an appliance in which the lower surfaces of the false teeth 58, 60 and 62 (or the lower rim of the appliance) will be at or slightly below the gingival margin to make the false teeth look like natural teeth in place in the gums. In addition, the design of the appliance will fully conceal the area of affixation and the abutment members 50 and 50'.

First and second coupling members means 66, 66' and 68, 68' are adapted to be respectively secured to the abutment members 50, 50' and the appliance 56 in the cavities formed by the complementary surfaces 54, 54', for removably retaining the appliance 56 on the tapered support surfaces 52, 52'. While the female coupling members 66, 66' may be provided separately and then soldered or otherwise attached to the apices 70, 70' of the tapered support surfaces 52, 52', it is preferable that the female coupling members be formed integral with and at the same time as the tapered support surfaces and abutment members are initially formed. This may be done by suitable casting or machining techniques.

As can be seen, the mating of the tapered support surfaces 52, 52' and the complementary surfaces 54, 54' of the appliance accurately guides the first and second coupling members into a coupling relationship to removably retain the appliance 56 on the tapered support surfaces. This design permits removal of the appliance by the wearer for hygenic and tissue stimulation purposes in the area concealed by the appliance, without having to make a trip to the dentist.

There are a number of coupling means that can be used to carry out this invention. For example, such coupling means are sold under trademarks or trade names SODENCO, ZEST, SHINER, JACKSON, etc. Other examples are shown in prior art patents, such as U.S. Pat. No. 3,797,114, cited hereinbefore. The coupling means illustrated and used in the preferred embodiments described herein is disclosed and described in detail in U.S. Pat. No. 4,540,367, issued on Sep. 10, 1985 to Josef M. Sulc. That disclosure and description in the Sulc patent is incorporated in this application by reference thereto. All of the coupling means suitable for use in this invention carry means for releasable engagement of the coupling means in response to placement of an appliance on the abutment member and removal of an appliance from the abutment member by the wearer, thereby permitting removal by the wearer for hygenic and tissue stimulation purposes in the area concealed by an appliance.

Each set of coupling means includes a female member 66 and a male member 68. The female member 66 is a cup-socket having an upstanding side wall 72. The outer surface of side wall 72 generally is slightly conical in outline, and merges with the apex 70 of the tapered support surface 52, with the merge line being set back from the tapered surface 52 to provide a shoulder to accomodate the bottom rim of the cup-shaped structure of the male member 68. The inner surface of the side wall of member 66 is contoured to form a necked-down region or constriction 74. The constriction may be characterized by a convex arc at about the midpoint of the length of the side wall 72 which merges, at its ends, in a concave arc toward the base and entry into the socket.

The female member 66 preferably is formed of a metallic material, such as a metal which conventionally finds use in the field of dentistry. Similarly, the abutment member 50 is also formed of the same metal, particularly if the female member 66 and the abutment member are formed together at the same time as an integral component.

The male member 68 preferably is formed of a plastic material, such as strong nylon. As noted in the referenced U.S. Pat. No. 4,540,367 the male member may be replaced by a new male member when wear requires replacement.

The male member 68 of the connector is also characterized by a cup-shaped structure. As such, the male member includes a wall 78 which extends from a base 80. In addition, a projection 82 extends from base 80 along the axis of wall 78. The projection 82 has an outer contour which generally is complementary to that of the inner surface of the side wall 72 of female member 66. To this end, the projection includes a constriction about the midpoint of its length which merges, at its ends, in a convex arc toward base 80 and the end of the projection. The constrictions allow for a snap fit retention.

The male member 68 is completed by a pair of ridges 84, 86 formed on the outer surface of wall 78. Each ridge extends completely around the wall. The ridges are spaced apart so that one ridge is near the base 80 and the other ridge is near the opening between the projection and the inner surface of the wall at the rim of the cup wall 78.

Although the above-noted female and male members are described only by the non-prime reference numbers of one set, the description is also applicable to prime reference numbers of the other set, since the components are identical.

The appliance 56, which in this case is a bridge, may be formed of a dental acrylic or cast in metal with porcelain fused to it, or a composite baked on to it. The appliance is removably mounted by a pair of male members which telescopically intercooperate with a pair of female members in mounting the appliance. Male members may be processed into dental acrylic, or may be received in metal receptacles 90, 90' which are processed in place in false teeth. Typically, this embedding occurs during the process of forming the appliance, which is carried out according to conventional techniques.

The receptacles 90, 90' provide internal surfaces that are complementary to the external surface of the walls and base of the male members. Thus, a pair of grooves 92, 94 and 92', 94' are formed around the internal surface of the wall of each receptacle, and the grooves are spaced to accomodate the ridges 84, 86 and 84', 86' of the male members 68, 68'. The receptacles 90, 90' may have serrated or roughened outer surfaces to maintain the embedded relationship for mechanical retention between the receptacles and the acrylic of the appliance.

As noted hereinbefore, the male members may be processed into acrylic. It is also possible to form the appliance or other suitable material so that the complementary surfaces 54, 54' are formed by acrylic. However, with the acrylics and other dental resins and plastics today, it is preferable to use the metal receptacles 90, 90' to insure that the appliance can tolerate the coring out replacement process for the male members, and to also use a cast metal for the receiving surfaces of the complementary surfaces 54, 54'. Thus, each cast metal receptacle would have a metal skirt depending therefrom to receive the tapered support surface of the abutment member.

When this invention is used with a bridge as shown in FIG. 3, or other appliance having a number of false teeth that is greater than the number of support points, it is standard technique to provide a connecting bar or pontic or member inside of the unsupported false teeth which extends or spans between support points. A support bar or pontic for false tooth 60 is shown extending between supported false teeth 58 and 62. Since the use of such a bar or span is standard, a detailed description need not be included as to how the bar or span is connected between the receptacles and skirts at each end of the bridge. Such techniques enable the casting of the receptacles, skirts and connecting bar all at the same time.

The appliance in U.S. Pat. No. 4,540,367, in which these removable-mounting coupling means are described, depends upon a saddle resting on gum tissue to provide stability and absorb chewing forces. However, one of the purposes of this invention is to do away with the use of saddles for the reasons set forth hereinbefore. In some instances, the patient's bone structure may be able to tolerate a totally rigid snap fit or connection by a removable mounting means. However, it is generally desirable to provide an alternative to a totally rigid connection. U.S. Pat. No. 4,540,367 partially addresses this question by providing an up-and-down space between the male and female members to prevent the breaking away of the cantilevered female member from an adjoining abutment tooth.

In addition to the just described up-and-down movement, this invention also addresses this problem by introducing cushioned resiliency in the coupling relationship by proper selection of a plastic for the male member. As noted hereinbefore, nylon may be used and may have the cushioned resiliency desired for a particular patient. In some instances it may be found that use of a plastic such as the CELCON brand acetal copolymer of the Celanese Corporation to obtain suitable density, resilience and flexibility. CELCON copolymer has a flexural modulus that closely approaches that of normal bone tissue, and would react in a manner to dissipate the forces under occlusal function to help avoid the problems of a totally rigid connection.

Abutment members 50, 50' carry means for affixing them to dental implants 40, 40'. In FIG. 3 steel or other metal shafts 100, 100' have screw threads formed thereon to be received in threaded bores 102, 102' of implants 40, 40'. In FIG. 5, the screw threaded shaft 104 is a shank of a screw having a head 106 carried in a bore 108 formed in an abutment member 110. The shank extends out of the bore 108 to be received by a threaded bore in a dental implant.

Referring to FIG. 4, there is illustrated an abutment member 114 for use with a partial tooth or tooth root. The shaft 116 may be cemented in place in bore 118. In some instances it may be possible to provide shaft 116 with screw threads so that the abutment may be removed in the future for further treatment or preparation of the tooth root or stub, or other repairs or restoration.

Referring now to FIG. 6 there is illustrated in a cross-sectional view an additional component of this invention. While the component shows a cross-section of plastic, it may also be made of metal as will be hereinafter described.

In addition to the standard techniques referred to hereinbefore for forming the appliance and the required complementary surfaces, it is possible to use receptacles 90, 90' that have been cast or formed in advance which have the required internal complimentary surfaces to save processing time and assure greater accuracy. Such a receptacle 124 is shown in FIG. 6. A receptacle may be an acrylic or other suitable plastic as shown by the sectional markings in FIG. 6, for processing in the appliance. The receptacle 124 may also be formed of metal to enable a retention of accurate complementary surfaces to mate with a metal abutment. If the receptacles are used in single tooth appliances, then the outer surfaces may be roughened to insure a good grip between the acrylic of the appliance and the receptacle. If used in a bridge, it is preferable that the receptacle is metal so that it can be soldered or cast or otherwise attached to the connecting bar or pontic or span.

FIG. 6 also represents the use of a receptacle that may be made of a soft plastic or other material that may be burned or melted out in the use of the lost-wax process for making castings to receive the second coupling means and the tapered support surface of the abutment member.

While the abutment member of this invention has been illustrated as used in a bridge with a plurality of dental implants, and alone with a partial tooth or tooth root, it should be kept in mind that uses with various dental appliances are envisioned. That is, a single artificial tooth, a full or partial denture, or any other such appliance using the support and connection features of this invention are intended to be covered.

This invention also covers a method for removably mounting a dental appliance in a person's mouth, including the step of forming an abutment member with a tapered support surface and fixing the abutment member in the mouth with the tapered support surface extending toward an opposing jaw. A further step includes forming the tapered support surface to be received in and mate with a complementary surface formed in an appliance, whereby said appliance is supported by said tapered support surface when seated thereon so that the appliance need not depend upon gum tissue for support, thereby enabling design of an appliance to fully conceal the area of affixation and the abutment member for esthetic purposes while providing the look of natural teeth.

The method includes the further step of securing first and second coupling means respectively to the abutment member and the appliance for removably retaining the appliance seated on the abutment member. A still further step includes positioning the first and second coupling means on the abutment member and the appliance so that the mating of the tapered and complementary surfaces during placement of an appliance on the abutment member accurately guides the coupling means into a coupling relationship which removably retains the appliance of the abutment member, said coupling relationship permitting removal of an appliance for hygenic and tissue stimulation purposes in the area concealed by the appliance.

The method may further include forming means carried by the abutment member for affixing the abutment member to a dental implant or to a partial tooth or tooth root in the mouth. The first coupling means is preferably formed integral with the apex of the tapered surface of the abutment member.

The method may also include forming a plurality of said abutment members and fixing said plurality of abutment members in the mouth in spaced relationship with respect to each other to provide spaced tapered support surfaces to be received in and mate with corresponding complementary surfaces formed in an appliance. It is also desirable to form the first and second coupling means at least partially with a material which provides cushioned resiliency in the coupling relationship.

While the choice of the specific components and their arrangement in the preferred embodiments described herein illustrate the results and advantages over the prior art, the invention is not limited to those specific components and their arrangement. Thus, the forms of the invention shown herein and described are to be taken as illustrative only, and changes in the components or their arrangement may be made without departing from the spirit and scope of this invention. There has been disclosed method and apparatus which differs from, provides functions not performed by, and has clear advantages over the prior art.

I claim:

1. Apparatus for removably mounting a dental appliance, such as an artificial tooth, a full or partial denture, a bridge or other appliance, in a mouth, comprising:
   (a) an abutment member adapted to be affixed in a mouth, said abutment member having a tapered support surface which extends away from the affixation area on one jaw toward the opposing jaw,
   (b) said tapered support surface being formed to be received in and mate with a complementary surface formed in an appliance to provide a support surface for such appliance so that the appliance need not depend upon gum tissue for support, thereby enabling design of an appliance to fully conceal the area of affixation and said abutment member for esthetic appearance while providing the look of natural teeth,
   (c) first and second coupling means adapted to be respectively secured to said abutment member and an appliance for removably retaining an appliance on said abutment member, said coupling means carrying means for releaseable engagement of said coupling means in response to placement of an appliance on said abutment member and removal of an appliance from said abutment member which can be accomplished by the wearer, thereby permitting removal by the wearer for hygenic and tissue stimulation purposes in the area concealed by an appliance,
   (d) the mating of said tapered support surface of said abutment member with the complementary receiving surface of an appliance accurately guiding said first and second coupling means into a coupling relationship to removably retain an appliance on said tapered support surface of an abutment member.

2. Apparatus as defined in claim 1 in which said abutment member carries means for affixing said abutment member to a dental implant fixed in a mouth.

3. Apparatus as defined in claim 1 in which said abutment member carries a screw-threaded shaft to be received in a threaded bore in a dental implant fixed in a mouth.

4. Apparatus as defined in claim 3 in which said screw-threaded shaft is a shank of a screw having a head carried in a bore formed in said abutment member, while said shank extends out of said bore to be received by a threaded bore in a dental implant.

5. Apparatus as defined in claim 1 in which said abutment member carries means for affixing said abutment member to a partial tooth or tooth root in a mouth.

6. Apparatus as defined in claim 5 in which said affixing means comprises a shaft for affixing said abutment member in a bore formed in a partial tooth or tooth root.

7. Apparatus as defined in claim 1 in which said first coupling means is connected to an apex of said tapered surface of said abutment member, and in which said second coupling means is to be secured in a cavity of an appliance having the complementary surface formed therein.

8. Apparatus as defined in claim 7 in which said connection of said first coupling means to said apex is accomplished by forming said first coupling means as an integral part of said apex of said tapered surface.

9. Apparatus as defined in claim 1 which further includes,
   (a) a plurality of said abutment members adapted to be affixed in the mouth in spaced relationship with respect to each other, each of said plurality of abutment members also having a tapered support surface extending away from the affixation area, each of said tapered support surfaces being formed to be received in and mate with a corresponding complementary surface formed in such appliance to provide a plurality of support surfaces for such appliance, and
   (b) means for removably retaining such appliance seated on said plurality of abutment members including a set of first and second coupling means associated with each of said abutment members, each set of first and second coupling means being respectively secured to the associated abutment member and such appliance,
   (c) the mating of each of said tapered support surfaces of said abutment members with the corresponding complementary receiving surfaces of such appliance accurately guiding each set of coupling means into a coupling relationship.

10. Apparatus as defined in claim 9 in which said first coupling means of each set is connected to an apex of said tapered surface of an associated abutment member, and in which said second coupling means of each set is adapted to be secured in a cavity having the corresponding complementary surface formed therein.

11. Apparatus as defined in claim 10 in which said connection of each of said first coupling means to an associated apex is accomplished by forming said first coupling means as an integral part of said associated apex.

12. Apparatus as defined in claim 1 in which said first and second coupling means includes means for introducing cushioned resiliency in the coupling relationship thereof in applications where it is undesirable to have a totally rigid coupling relationship which would directly transmit all force received by such appliance to a jaw to which said abutment member is attached.

13. Apparatus as defined in claim 1 in which said second coupling means is to be secured in a cavity of an appliance having the complementary surface formed therein, and which further includes a receptacle for receiving said second coupling means, said receptacle having a skirt attached thereto which defines the desired complementary surface for the tapered support surface of said abutment member, said combination receptacle-skirt being adapted to be embedded in said appliance during formation thereof.

14. Apparatus as defined in claim 1 in which said second coupling means is to be secured in a cavity of an appliance having the complementary surface formed therein, and which further includes a plastic model form to be placed over a second coupling means which is in a coupling relationship with a first coupling means connected to an apex of a tapered support surface of an abutment member, said model form completely covering said second coupling means and said tapered support surface to enable placement of said form in an appliance cavity to be burned or melted out in a lost-wax process to provide a mold for a casting which will have an interior surface which is complementary to the exterior surface of said second coupling means and said tapered support surface of said abutment means.

15. A method for removably mounting a dental appliance such as an artificial tooth, a full or partial denture, a bridge or other appliance in a mouth, comprising the steps of:
   (a) forming an abutment member with a tapered support surface and fixing said abutment member in the mouth with the tapered surface extending toward an opposing jaw,
   (b) forming said tapered support surface to be received in and mate with a complementary surface formed in an appliance, whereby said appliance is supported by said tapered support surface when seated thereon so that said appliance need not depend upon gum tissue for support, thereby enabling design of an appliance to fully conceal the area of affixation and said abutment member for esthetic purposes while providing the look of natural teeth, (c) securing first and second coupling means respectively to said abutment member and said appliance for removably retaining said appliance seated on said abutment member, and (d) positioning said first and second coupling means on said abutment member and said appliance so that the mating of said tapered and complementary surfaces during placement of an appliance on said abutment member accurately guides said coupling means into a coupling relationship which removably retains said appliance on said abutment member, said coupling relationship permitting removal of an appliance by the wearer for hygenic and tissue stimulation purposes in the area concealed by the appliance.

16. A method as defined in claim 15 which further includes forming means carried by said abutment member for affixing said abutment member to a dental implant fixed in the mouth.

17. A method as defined in claim 15 which further includes forming means carried by said abutment member for affixing said abutment member to a partial tooth or tooth root.

18. A method as defined in claim 15 in which said first coupling means is formed integral with the apex of said tapered surface of said abutment member.

19. A method as defined in claim 15 which further includes forming a plurality of said abutment members and fixing said plurality of abutment members in the mouth in spaced relationship with respect to each other to provide spaced tapered support surfaces to be received in and mate with corresponding complementary receiving surfaces formed in an appliance.

20. A method as defined in claim 15 in which said first and second coupling means are formed at least partially with a material which provides cushioned resiliency in the coupling relationship thereof.

* * * * *